(12) United States Patent
Hayden et al.

(10) Patent No.: US 9,241,679 B2
(45) Date of Patent: Jan. 26, 2016

(54) METHOD AND APPARATUS FOR FILTERING HIGH-FREQUENCY ELECTROMAGNETIC BEAMS AND IRRADIATION APPARATUS OR DEVICE FOR IRRADIATING AN OBJECT

(71) Applicant: SIEMENS AKTIENGESELLSCHAFT, Munich (DE)

(72) Inventors: Oliver Hayden, Herzogenaurach (DE); Manfred Ruehrig, Lauf A.D. Pegnitz (DE); Frank Sauer, Princeton, NJ (US); Reiner Franz Schulz, Erlangen (DE); Sandro Francesco Tedde, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 70 days.

(21) Appl. No.: 13/927,633

(22) Filed: Jun. 26, 2013

(65) Prior Publication Data
US 2013/0343516 A1 Dec. 26, 2013

Related U.S. Application Data

(60) Provisional application No. 61/664,331, filed on Jun. 26, 2012.

(51) Int. Cl.
*A61B 6/10* (2006.01)
*G21K 1/10* (2006.01)
(Continued)

(52) U.S. Cl.
CPC .............. *A61B 6/107* (2013.01); *A61B 6/032* (2013.01); *A61B 6/06* (2013.01); *A61B 6/4035* (2013.01); *A61B 6/542* (2013.01); *G21K 1/10* (2013.01); *G21K 5/04* (2013.01)

(58) Field of Classification Search
CPC ...... A61B 6/032; A61B 6/107; A61B 6/4035; A61B 6/06; A61B 6/542; G21K 1/10; G21K 5/04
USPC ................................. 378/16, 62, 64, 145, 156
See application file for complete search history.

(56) References Cited

U.S. PATENT DOCUMENTS

| 4,580,113 A | * | 4/1986 | Pinson | 333/81 B |
| 6,188,749 B1 | * | 2/2001 | Schiller et al. | 378/158 |

(Continued)

FOREIGN PATENT DOCUMENTS

| FR | 2244187 A1 | * | 4/1975 | ............... G02F 1/30 |
| FR | 2599886 A1 | * | 12/1987 | ............... G21K 4/00 |

OTHER PUBLICATIONS

Giri et. al., Synthesis and characterizations of water-based ferrofluids of substituted ferrites for biomedical applications, Mar. 2008, Journal of Magnetism and Magnetic Materials, vol. 320, No. 5, p. 725, 728.*

(Continued)

*Primary Examiner* — David J Makiya
*Assistant Examiner* — Julio M Duarte-Carvajalino
(74) *Attorney, Agent, or Firm* — Laurence Greenberg; Werner Stemer; Ralph Locher

(57) ABSTRACT

A method and an apparatus for filtering radio-frequency electromagnetic beams, in particular x-rays, include a fluid container containing a ferrofluid which at least partially absorbs the electromagnetic beams. A distribution of the ferrofluid within the fluid container can be varied by using an applied magnetic gradient field. An irradiation apparatus and a device for irradiating an object are also provided.

19 Claims, 9 Drawing Sheets

(51) Int. Cl.
*G21K 5/04* (2006.01)
*A61B 6/03* (2006.01)
*A61B 6/06* (2006.01)
*A61B 6/00* (2006.01)

(56) References Cited

U.S. PATENT DOCUMENTS 7,308,073 B2 * 12/2007 Tkaczyk et al. ............. 378/16
2007/0071176 A1 * 3/2007 Main et al. ................. 378/207

OTHER PUBLICATIONS

Tan et. al., Formation and manipulation of ferrofluid droplets at a microfluidic T-junction, Mar. 2010, J. Micromech. Microeng., vol. 20, p. 1, 2, 4, 7.*
Pant et. al., Microwave Absorption Studies on Ferrofluid-Conducting Polymer Composite, Oct. 2005, presented at XXVIIIth General Assy of Int'l Union of Radio Science, New Dehli, India.*
Machine translation of FR2244187.*

* cited by examiner

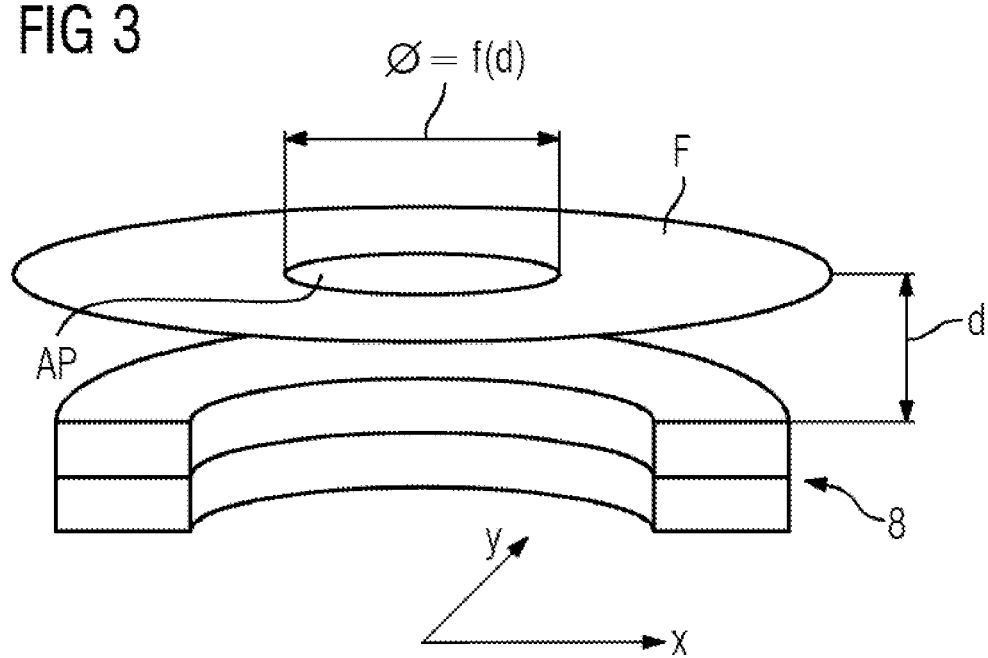

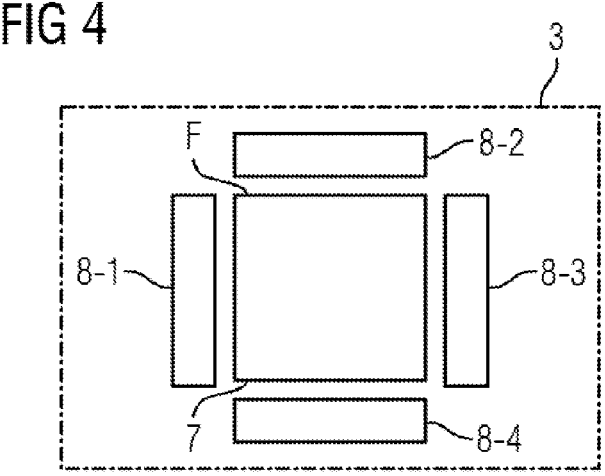
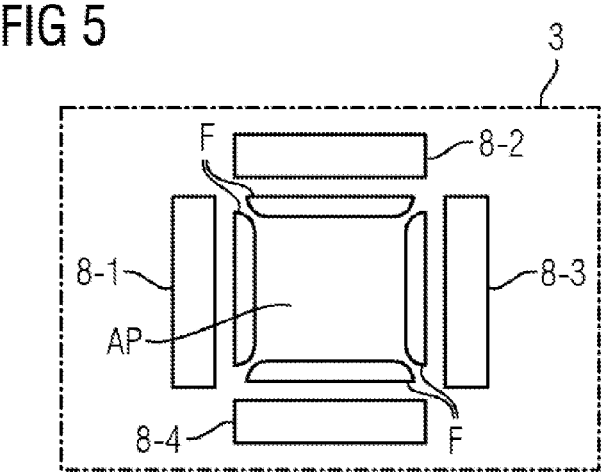
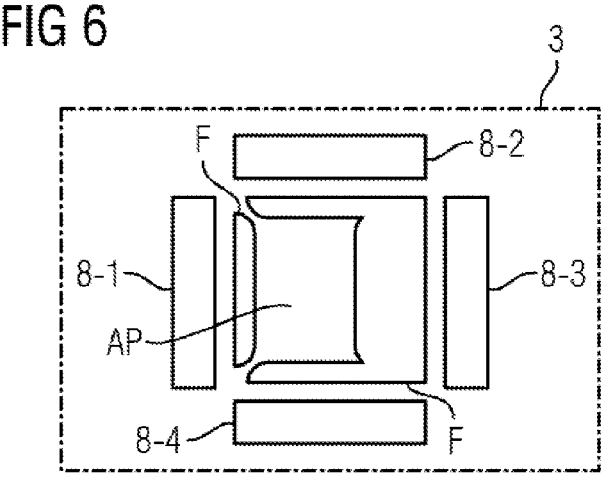

METHOD AND APPARATUS FOR FILTERING HIGH-FREQUENCY ELECTROMAGNETIC BEAMS AND IRRADIATION APPARATUS OR DEVICE FOR IRRADIATING AN OBJECT

CROSS-REFERENCE TO RELATED APPLICATION

This application claims the priority, under 35 U.S.C. §119(e), of U.S. Provisional Patent Application No. 61/664,331, filed Jun. 26, 2012; the prior application is herewith incorporated by reference in its entirety.

BACKGROUND OF THE INVENTION

Field of the Invention

The invention relates to a method and an apparatus for filtering high-frequency electromagnetic beams and, in particular, to a filter apparatus for filtering x-rays, as well as to a corresponding irradiation apparatus and a corresponding irradiation device.

In many applications it is necessary to filter high-frequency electromagnetic beams. In the case of medical devices, exposing a patient to an excessively high dose of electromagnetic radiation can result in damage to the patient. Reducing exposure to x-ray dosages is always of critical importance in radiological imaging methods. The conventional approach entails partially masking out x-rays in a projection method by using mechanical baffles.

FIG. 1 shows a conventional mechanical aperture which employs metal plates for partially shading an organism or body. The high-frequency electromagnetic radiation originating from a radiation source SQ is partially shaded by shifting the metal plates MP or mechanical baffles so that the electromagnetic beams are incident on the body of a patient P that is to be examined in a relatively small region only. A film that is to be developed or a camera for recording the electromagnetic beams passing through the patient P can be located beneath the patient P as a detector D. The baffles or metal plates MP are formed of highly absorbent materials such as lead, for example, and absorb virtually all of the electromagnetic radiation impinging thereon.

The mechanical aperture according to the prior art shown in FIG. 1 has several significant disadvantages. Firstly, the plates or baffles used therein are relatively heavy and large and correspondingly difficult to operate. A further disadvantage is that the absorption of the high-frequency electromagnetic beams emitted by the radiation source SQ cannot be controlled. This means that in the remaining free space between the metal plates or baffles the high-frequency electromagnetic beams pass through unfiltered and strike the patient's body. For this reason, uniform prefiltering can be performed in a prefilter.

BRIEF SUMMARY OF THE INVENTION

It is accordingly an object of the invention to provide a method and an apparatus for filtering high-frequency electromagnetic beams and an irradiation apparatus or device for irradiating an object, which overcome the hereinafore-mentioned disadvantages of the heretofore-known methods, apparatuses and devices of this general type and in which, in particular, the radiation absorption is adjustable and/or controllable.

With the foregoing and other objects in view there is provided, in accordance with the invention, a filter apparatus for filtering high-frequency electromagnetic beams. The filter apparatus comprises a fluid container containing a ferrofluid at least partially absorbing the electromagnetic beams. The ferrofluid has a distribution within the fluid container being variable by an applied magnetic gradient field.

The filter apparatus according to the invention is suitable, in particular, for filtering x-rays.

An advantage of the filter apparatus according to the invention is that a uniform prefilter can be replaced. It is furthermore possible to set a location-dependent radiation dosage distribution.

In accordance with another feature of the filter apparatus of the invention, the ferrofluid has ferromagnetic particles that are suspended in a carrier medium, in particular oil.

In accordance with a further feature of the filter apparatus of the invention, a liquid is provided in the fluid container in addition to the ferrofluid. The liquid is not miscible with the carrier medium of the ferrofluid and exhibits a considerably lower level of absorption with respect to the electromagnetic beams being used.

In one possible embodiment variant the immiscible radiation-transparent liquid is water.

In another possible embodiment variant the immiscible radiation-transparent liquid is alcohol.

In accordance with an added feature of the filter apparatus of the invention, the magnetic gradient field is generated by magnets which are disposed around the fluid container.

In accordance with an additional feature of the filter apparatus of the invention, the magnets are formed by electromagnets.

In accordance with yet another feature of the filter apparatus of the invention, the generated field strength of the electromagnets is adjustable.

In accordance with yet a further feature of the filter apparatus of the invention, permanent magnets can be used having a magnetic field strength at the location of the fluid container which can be varied by way of the distance from the fluid container.

In accordance with yet an added feature of the filter apparatus of the invention, a filter property of the ferrofluid contained in the fluid container can be set with respect to the absorption of the high-frequency electromagnetic beams.

In accordance with yet an additional feature of the filter apparatus of the invention, the filter property of the ferrofluid contained in the fluid container can be set with respect to the absorption of the high-frequency electromagnetic beams through a selection of magnetic particles or a mixture of different magnetic particles.

In accordance with again another feature of the filter apparatus of the invention, the filter property of the ferrofluid contained in the fluid container with respect to the absorption of the high-frequency electromagnetic beams can be adjusted by using admixtures of nonmagnetic particles into the ferrofluid.

In accordance with again a further feature of the filter apparatus of the invention, the filter property of the ferrofluid contained in the fluid container can be set with respect to the absorption of the high-frequency electromagnetic beams by changing a percentage by volume of magnetic and nonmagnetic particles in the ferrofluid as well as by varying the volume of the ferrofluid contained in the container.

With the objects of the invention in view, there is also provided an irradiation apparatus for irradiating an object with high-frequency electromagnetic beams, in particular with x-rays. The apparatus comprises a radiation source for generating the high-frequency electromagnetic radiation, in particular x-rays, as well as a filter apparatus for filtering high-frequency electromagnetic beams, the filter apparatus having a fluid container containing a ferrofluid at least partially absorbing the electromagnetic beams, and the ferrofluid having a distribution within the fluid container being variable by an applied magnetic gradient field.

With the objects of the invention in view, there is furthermore provided an irradiation device for irradiating an object with high-frequency electromagnetic beams, in particular with x-rays. The irradiation device comprises an irradiation apparatus for irradiating an object with high-frequency electromagnetic beams having a radiation source for generating the high-frequency electromagnetic radiation as well as a filter apparatus for filtering high-frequency electromagnetic beams. The filter apparatus has a fluid container containing a ferrofluid which at least partially absorbs the electromagnetic beams, the ferrofluid having a distribution within the fluid container being variable by an applied magnetic gradient field. The irradiation device additionally has a patient receiving compartment for accommodating a patient as an object as well as a radiation detector disposed in the patient receiving compartment for registering or detecting or recording the electromagnetic beams passing through the patient.

In accordance with another feature of the irradiation device of the invention, the distribution of the ferrofluid within the fluid container is set as a function of a detected position of the patient contained in the patient receiving compartment.

In accordance with a further feature of the irradiation device of the invention, the irradiation apparatus contained therein is disposed so as to be rotatable around the patient receiving compartment of the irradiation device.

In accordance with an added feature of the irradiation device of the invention, the radiation detector has a camera.

In accordance with an additional feature of the irradiation device of the invention, the radiation detector has an exposable film.

In accordance with yet another feature of the irradiation device of the invention, the fluid container has a so-called bow-tie geometry.

In accordance with yet a further feature of the irradiation device of the invention, the distribution of the ferrofluid contained inside the fluid container can be varied relative to a projection axis of the irradiation device by using the applied magnetic gradient field.

With the objects of the invention in view, there is concomitantly provided a method for filtering high-frequency electromagnetic beams, which comprises varying a distribution of a ferrofluid at least partially absorbing electromagnetic beams by using an applied magnetic gradient field.

Other features which are considered as characteristic for the invention are set forth in the appended claims.

Although the invention is illustrated and described herein as embodied in a method and an apparatus for filtering high-frequency electromagnetic beams and an irradiation apparatus or device for irradiating an object, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Possible embodiment variants of the apparatus according to the invention for filtering high-frequency electromagnetic beams, of the irradiation apparatus according to the invention for irradiating an object with high-frequency electromagnetic beams, as well as of the irradiation device according to the invention, are explained in more detail hereinbelow with reference to the attached figures.

BRIEF DESCRIPTION OF THE SEVERAL VIEWS OF THE DRAWING

FIG. 3 is a perspective view intended to explain a mode of operation of a filter apparatus according to the invention;

FIGS. 4, 5 and 6 are top-plan views of an exemplary embodiment of the filter apparatus according to the invention;

DESCRIPTION OF THE INVENTION

Figure 1:
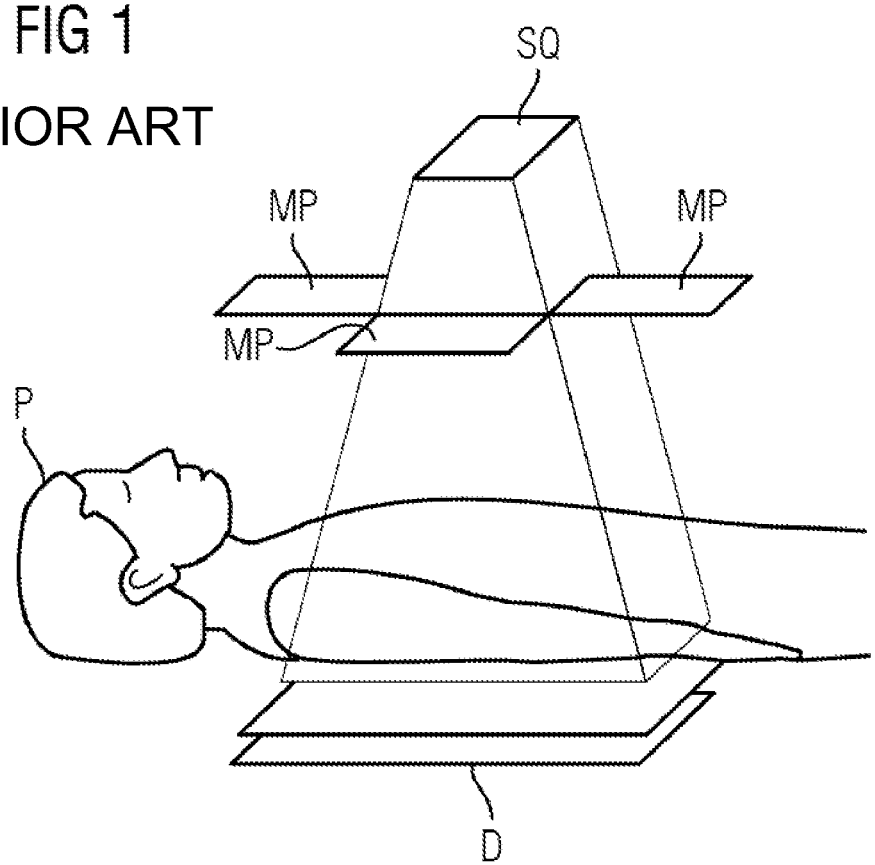
FIG. 1 is a diagrammatic, perspective view of a conventional mechanical aperture according to the prior art.
Figure 2:
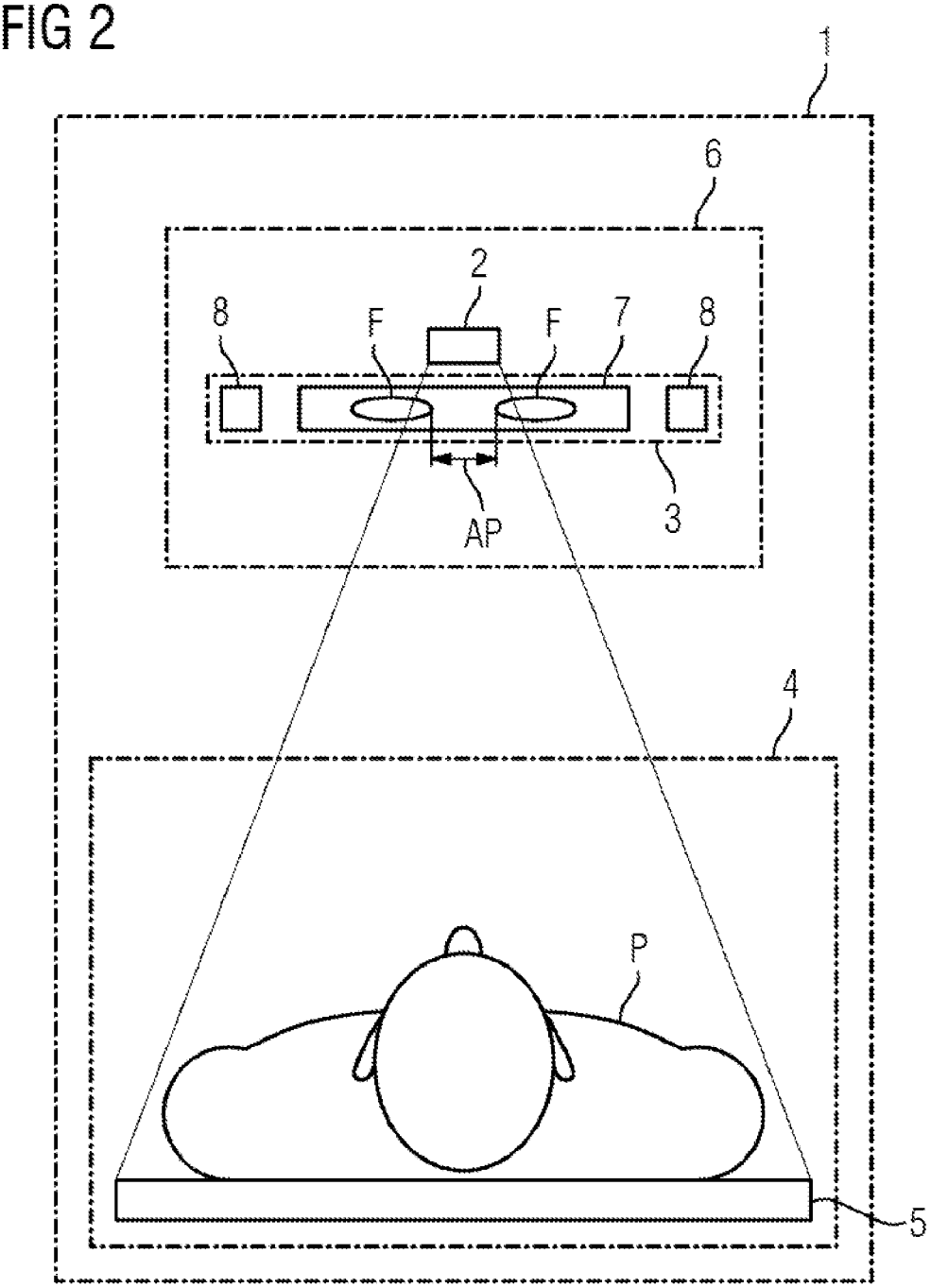
FIG. 2 is a block diagram intended to illustrate an exemplary embodiment of an irradiation device according to the invention which contains a filter apparatus according to the invention for filtering high-frequency electromagnetic beams.

Referring now to the figures of the drawings in detail and first, particularly, to FIG. 2 thereof, there is seen an irradiation device 1 according to the invention which has a radiation source 2 for generating high-frequency electromagnetic beams, in the illustrated exemplary embodiment. For example, the radiation source 2 can be an x-ray radiation source for generating x-rays. A filter apparatus 3 for filtering high-frequency electromagnetic beams, in particular for filtering x-rays, is also to be seen in FIG. 2. The irradiation device 1 furthermore has a patient receiving compartment 4 for accommodating a patient P as an irradiation object. The head of the patient P and the two adjacent arms of the patient P are indicated in FIG. 2. The irradiation device 1 additionally has a radiation detector 5 for registering the electromagnetic beams passing through the patient P.

Figure 9:
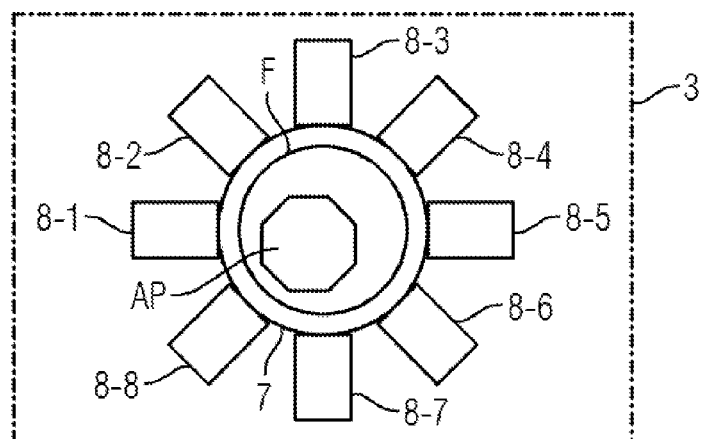

The radiation source 2 for generating the high-frequency electromagnetic beams and the filter apparatus 3 in combination form an irradiation apparatus 6. In a possible embodiment variant, the irradiation apparatus 6 is disposed so as to be rotatable around the patient receiving compartment 4 of the irradiation device 1, as shown in FIG. 9. The patient P shown in FIG. 2 can be positioned on a couch under which the radiation detector 5 is located. The radiation detector 5 can, for example, be an exposable film or the like. Alternatively, the radiation detector 5 can also be a camera for recording the beams passing through the body of the patient P.

The irradiation apparatus 6 includes the radiation source 2 on one hand and the filter apparatus 3 on the other hand. The filter apparatus 3, in particular its fluid container, can be replaceable. This means that the filter apparatus 3 can be removed from the irradiation device 1 and replaced by another filter apparatus 3'. The filter apparatus 3 has a fluid container 7 containing a ferrofluid F which at least partially or completely absorbs the electromagnetic beams emitted by the radiation source 2. At the same time the distribution of the ferrofluid F within the fluid container 7 of the filter apparatus 3 can be varied by using an applied magnetic gradient field. In a possible embodiment variant the ferrofluid F contained in the fluid container can have ferromagnetic nanoparticles which are contained in a carrier medium. The carrier medium can, for example, be oil or the like. Preferably, a transparent liquid A, which is not miscible with the carrier medium of the ferrofluid, is also contained in the fluid container 7 in addition to the ferrofluid F. The transparent liquid A is, for example, water or alcohol. Accordingly, the ferrofluid F is preferably present in the fluid container 7 in a two-phase system, wherein the ferrofluid F forms a first phase which at least partially absorbs electromagnetic radiation, for example x-ray radiation, and the second phase, for example alcohol, is at least partially transparent with regard to the electromagnetic radiation. In this configuration, the magnetic particles of the first phase themselves can be absorbent or the magnetic particles can be suspended in a carrier medium which is absorbent with respect to the electromagnetic beams. A combination of both properties is also possible.

The magnetic gradient field is preferably generated by using magnets 8 which are disposed around the fluid container 7. For example, the magnets can be disposed around the fluid container 7 in an annular configuration. In a possible embodiment variant the magnets 8 are electromagnets, the generated field strength of which is adjustable in each case. In another possible embodiment variant the distance from the electromagnets 8 to the fluid container 7 can be variable in addition. Alternatively, the magnets 8 can also be permanent magnets disposed at a distance from the fluid container 7 of the filter apparatus 3 which is variable. When permanent magnets are used, the size and position of an aperture AP can be controlled or adjusted by positioning the magnets 8 relative to the fluid container 7 or, as the case may be, to the ferrofluid F contained therein. If electromagnets are used as magnets 8, the positioning of the poles around the fluid container 7 preferably remains constant. The size and position of the aperture are specified by the gradient field strength of the electromagnet system.

In a possible embodiment variant of the filter apparatus 3, a filter property of the ferrofluid F contained in the fluid container 7 of the filter apparatus 3 can be adjusted with respect to the absorption of the high-frequency electromagnetic radiation. Alternatively, the filter property can also be varied by removing the filter apparatus 3 from the irradiation device 1 and replacing it with another filter apparatus.

In another possible embodiment variant of the filter apparatus 3 according to the invention, the filter property of the ferrofluid F contained in the fluid container can be adjusted with respect to the absorption of the high-frequency electromagnetic radiation by selecting magnetic particles or a mixture of different magnetic particles.

In another possible embodiment variant of the filter apparatus 3 according to the invention, the filter property of the ferrofluid F contained in the fluid container 7 can be adjusted or varied by the admixtures of nonmagnetic particles into the ferrofluid F.

In another possible embodiment, variant the filter property of the ferrofluid contained in the fluid container 7 can be adjusted or varied by changing a percentage by volume of magnetic and nonmagnetic particles in the ferrofluid F as well as by varying the volume of the ferrofluid F contained in the fluid container 7.

Ferrofluids F can be formed, for example, of 5% solid fraction and can have 10-nm large particles composed of $\gamma$-$Fe_2O_3$ (maghemite) or $Fe_3O_4$ (magnetite). The ferrofluid can furthermore include 10% surfactants for stabilizing the suspension and 85% carrier material or carrier medium. The carrier medium can, for example, contain organic solvents, water or oils. Lecithins, sugar-based surfactants and/or alkyl glycosides or synthetic alkanes or olefins, for example, are used as surface activators or surfactants.

FIG. 3 diagrammatically shows an exemplary embodiment of a filter apparatus 3 according to the invention having an iris-shaped aperture. The aperture AP is adaptive, in that the distribution of the ferrofluid F within the fluid container 7 is varied by the applied magnetic gradient field. The radiation-absorbing fraction of the ferrofluid F contained in the fluid container 7 forms a radiation-absorbing area at the edge of the fluid container 7, with the result that at that point, depending on the absorption characteristics of the ferrofluid, fewer to no electromagnetic beams can pass through. An area which does not absorb the electromagnetic beams or absorbs them to a lesser extent forms in the center of the fluid container 7 so that the electromagnetic beams originating from the radiation source 2 can pass through the iris-shaped region. In the diagram shown in FIG. 3, the non-absorbing aperture AP or area, which for example is transparent to x-rays, has a diameter Ø (d) which is dependent on a distance d between the fluid container 7 and an annular magnet 8. In the exemplary embodiment shown in FIG. 3, the magnetic gradient field is generated by using an annular permanent magnet 8. The permanent magnet 8 is separated by a distance d from the ferrofluid F contained in the fluid container 7. By varying the distance d between the permanent magnet 8 and the fluid container 7, it is thereby possible to set or adjust the diameter 0 (d) of the aperture. For example, the position or orientation of the permanent magnet 8 can be set relative to the fluid container 7 by using an actuator, with the actuator being adjusted by using a control apparatus or controller. The controller, for its part, can be connected to the radiation detector 5 of the irradiation device 1, with the radiation detector 5 registering the electromagnetic radiation arriving there and reporting the same to the controller. Based on the registered electromagnetic radiation, the controller can then vary the distance d in order to change the magnetic gradient field and so perform an adjustment. In the exemplary embodiment shown in FIG. 3, the controller or adjusting apparatus can move the magnet 8 in the z-direction in order to vary the distance d between the fluid container 7 and the magnet 8. It is furthermore possible for the controller to shift the position of the magnet or permanent magnet 8 in the xy plane in order to thereby produce a corresponding displacement of the iris-shaped aperture AP.

FIGS. 4-9 show views from above onto exemplary embodiments of the filter apparatus 3 according to the invention for filtering high-frequency electromagnetic beams.

As can be discerned from the embodiment variant shown in FIGS. 4-6, the fluid container 7 of the filter apparatus 3 is built in a square shape in this exemplary embodiment and is surrounded by four electromagnets 8-1, 8-2, 8-3, 8-4 in the west, north, east and south direction, respectively. The magnets 8-1, 8-2, 8-3, 8-4 are preferably electromagnets, the generated field strength of which is adjustable in each case. In this configuration the individual poles or electromagnets 8-1, 8-2, 8-3, 8-4 are preferably controllable independently of one another. This also enables the focus of the aperture AP to be shifted, as shown for example in FIGS. 5 and 6.

Figure 7:
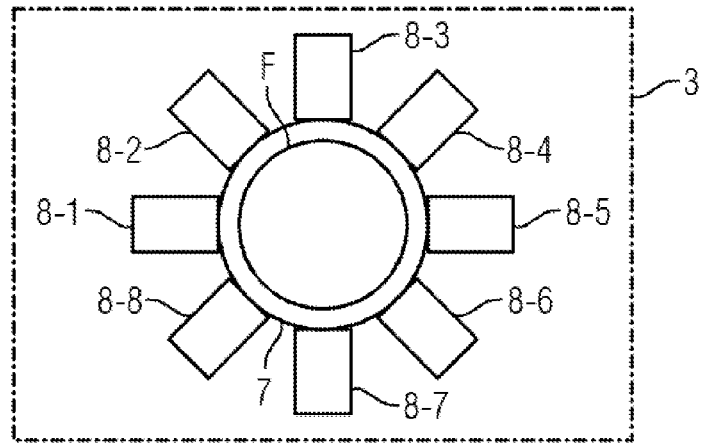
FIGS. 7, 8 and 9 are top-plan views of a further exemplary embodiment of the filter apparatus according to the invention.
Figure 8:
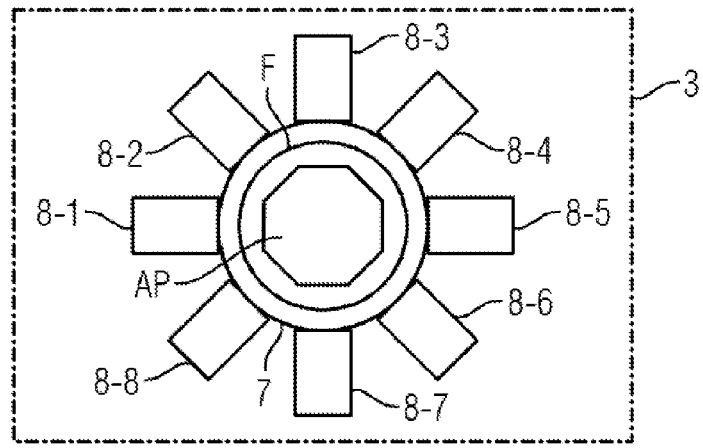

In the embodiment variant shown in FIGS. 7-9, the base area of the fluid container 7 is circular and is enclosed in a ring shape by eight different electromagnets or poles 8. The number of electromagnets 8 encircling the fluid container 7 can vary in both embodiment variants shown in FIGS. 4-6 and 7-9. In the embodiment variant shown in FIGS. 7-9, the different electromagnets 8-1 to 8-8 or poles can also be controlled or switched independently of one another.

The positioning of the electromagnets 8 shown in FIGS. 4-9, preferably remains constant. The size and position of the aperture is specified by the gradient field strength of the individual poles or electromagnets 8. Since the aperture system functions or is set on the basis of a volume conservation of the ferrofluidic phase, a gradually increasing ferrofluid layer thickness develops toward the walls of the fluid container 7 as a function of the gradient field strength. If the electromagnets 8 are switched off, the radiation-absorbing fluid layer is distributed over the entire cross-section of the fluid container 7, as shown in FIGS. 4 and 5. If the magnets 8 generate a relatively strong gradient field, the ferrofluid film is distributed as shown in FIGS. 5 and 8, i.e. a radiation-permeable aperture forms in the center of the fluid container 7 and the radiation-absorbing fraction of the ferrofluid F collects at the edge of the fluid container 7. Depending on the setting of the field strengths generated by the magnets 8, the position of the aperture AP within the fluid container 7 can also be shifted in different directions, as shown in FIGS. 6 and 9. In FIG. 6, for example, the focus of the aperture AP is located close to the magnet 8-1 and at a relatively great distance from the oppositely disposed magnet 8-3 because of the difference in the field strengths generated by the electromagnets 8-1 and 8-3. In the example shown in FIG. 6, the electromagnets 8-2, 8-4 have an approximately equal electromagnetic field strength. In the example shown in FIG. 9, the electromagnetic field strengths of the oppositely disposed electromagnets 8-8 and 8-4, for example, are different. The focus of the aperture AP is therefore located offset from the center in the direction of that electromagnet 8 which produces a higher electromagnetic field strength.

Figure 10:
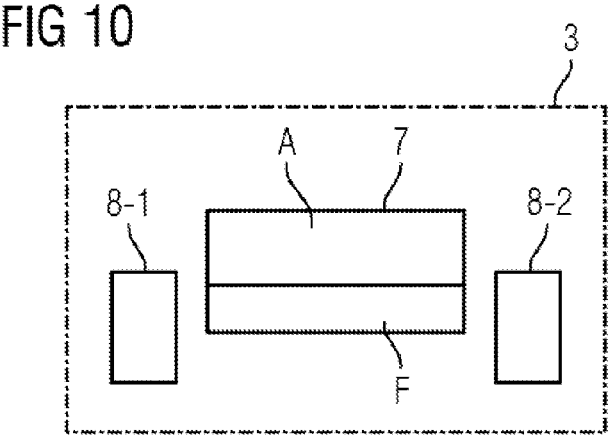
FIGS. 10, 11 and 12 are sectional side views intended to explain the mode of operation of a filter apparatus according to the invention.
Figure 11:
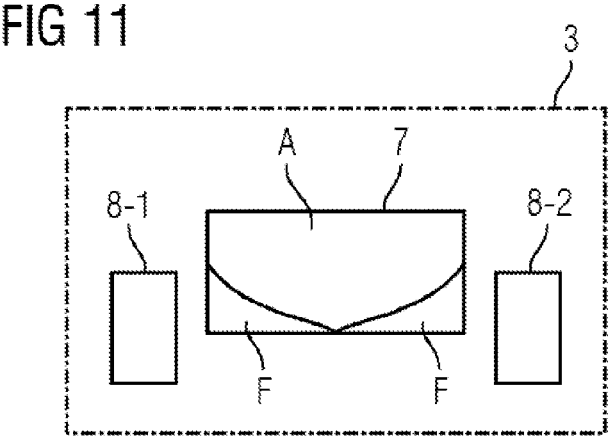
Figure 12:
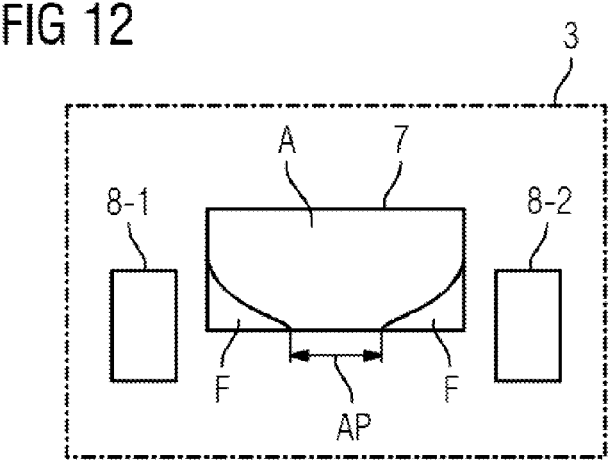

FIGS. 10-12 show sectional side views through an exemplary embodiment of the filter apparatus 3 according to the invention. The fluid container 7 is located between two electromagnets 8-1, 8-2 and contains a ferrofluid F as well as a liquid having lower absorption properties, for example alcohol A, which is not miscible with the carrier medium of the ferrofluid F. Alternatively, water can also be used as the immiscible medium. The ferrofluid F contains ferromagnetic particles that are suspended in a carrier medium, for example oil. The ferrofluid F and the immiscible liquid A accordingly form a two-phase immiscible system.

In FIG. 10, the two electromagnets 8-1, 8-2 are switched off, causing the ferrofluid F to be distributed uniformly over the floor of the fluid container 7.

In FIG. 11, the two electromagnets 8-1, 8-2 are switched on and generate an electromagnetic field, as a result of which the ferrofluid F is displaced toward the outer walls of the fluid container 7, with an aperture AP having a small diameter Ø forming on the floor of the fluid container 7. If, as shown in FIG. 12, the electromagnetic field strength of the electromagnets 8-1, 8-2 is increased further, the ferrofluid F is displaced further toward the outer walls of the fluid container 7, with the result that the diameter Ø of the aperture AP increases in the center on the floor of the fluid container 7. In this way, the electromagnetic radiation passing through the filter apparatus 3 can fall onto an object located therebelow. In contrast, in the situation shown in FIG. 10 with electromagnets 8-1, 8-2 switched off, the electromagnetic radiation is absorbed completely by the ferrofluid F and cannot impinge on an object located therebelow, in particular a patient P.

Figure 13:
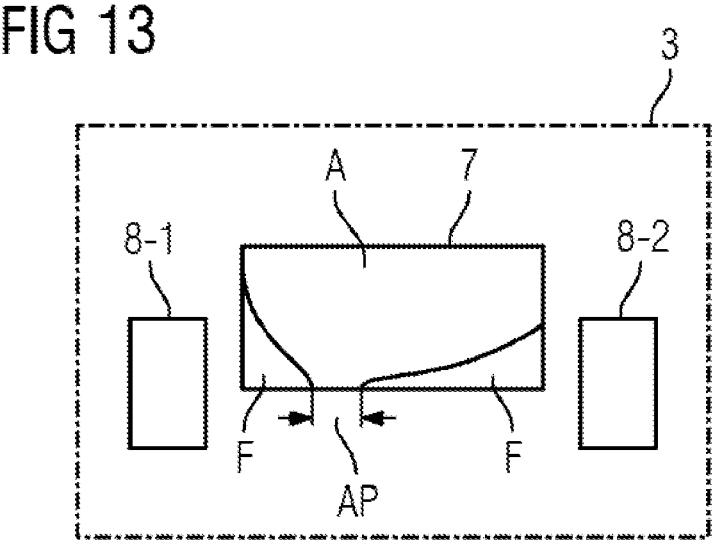
FIG. 13 is a sectional side view intended to explain a further filter apparatus according to the invention.

FIG. 13 shows a situation in which the electromagnetic field strength of the two oppositely disposed electromagnets 8-1, 8-2 is different. In the example shown in FIG. 13, the first electromagnet 8-1 has a higher electromagnetic field strength than the second electromagnet 8-2, so the focus of the aperture AP is shifted toward the first electromagnet 8-1.

Figure 14:
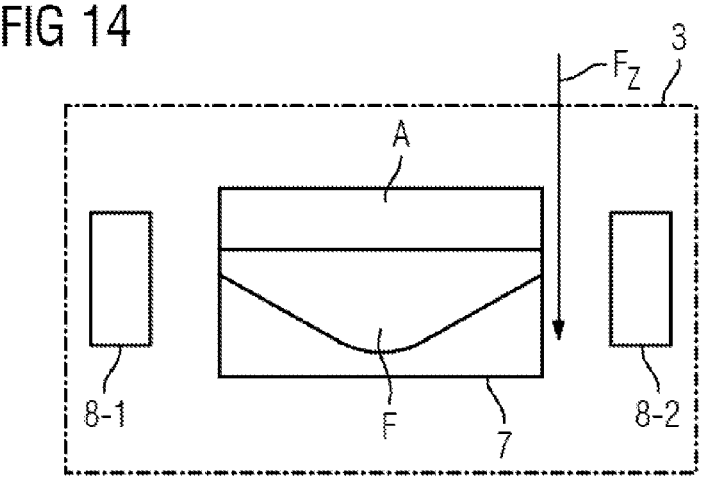
FIGS. 14, 15 and 16 are sectional side views of a further exemplary embodiment of a filter apparatus according to invention.
Figure 15:
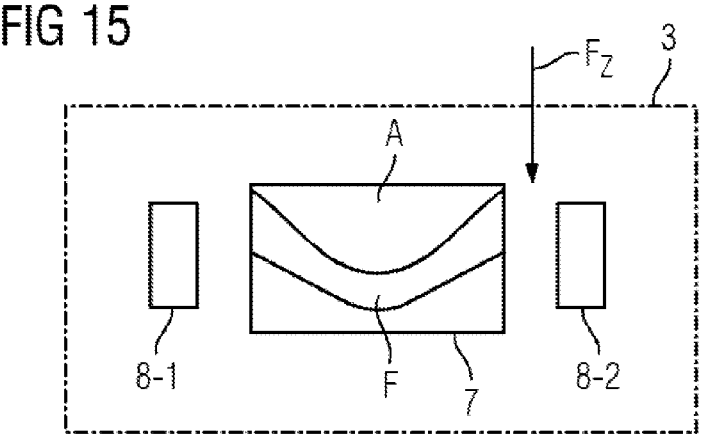
Figure 16:
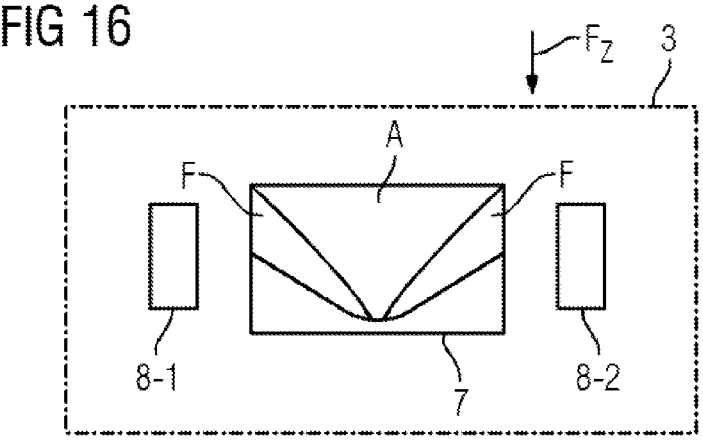

FIGS. 14-16 show another possible exemplary embodiment of the filter apparatus 3 according to the invention for filtering high-frequency electromagnetic beams. In the embodiment variant shown in FIGS. 14-16, the fluid container 7 has a so-called bow-tie geometry. In this case, the floor of the fluid container 7 is not flat, as in the embodiment variants shown in FIGS. 4-13, but instead is curved, with the result that the ferrofluid F has a greater layer thickness in the center of the fluid container 7 than at the edge of the fluid container 7. A liquid having reduced absorption properties, for example alcohol A, which is not miscible with the carrier medium of the ferrofluid F, is located above the ferrofluid F as shown in FIGS. 14-16. Two electromagnets 8-1, 8-2 which can be switched on and off and which have an electromagnetic field strength that can be adjusted, are located at the sides of the ferrofluid container 7. A radiation source 2, in particular an x-ray radiation source, can be positioned above the fluid container 7. In a possible embodiment variant, the radiation source 2 is rotated together with the bow-tie-shaped fluid container 7 around a patient space 4 of an irradiation device 1, thereby generating a centrifugal force F. In FIG. 14, the two electromagnets 8-1, 8-2 are switched off. FIG. 15, in contrast, shows a situation in which the two electromagnets 8-1, 8-2 are switched on. As can be seen from FIG. 15, the ferrofluid F is displaced toward the outer walls of the fluid container 7 due to the electromagnetic gradient field. If the electromagnetic field strength of the electromagnets 8-1, 8-2 is increased further, the situation depicted in FIG. 16 results, where an aperture AP opens on the floor of the fluid container 7, in such a way that the floor of the fluid container 7 lies in the center underneath the transparent alcohol A. The bow-tie filter shown in FIGS. 14-16 can be used in the radiation or x-ray source in order to compensate for attenuation due to the body of the patient P. The bow-tie filter can be used, for example, in a CT device or the like.

Figure 17:
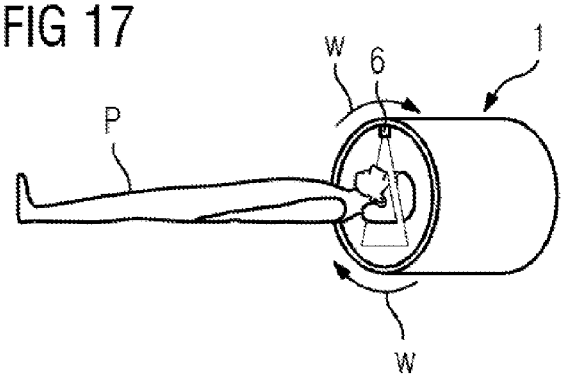
FIG. 17 is a perspective view intended to illustrate a possible exemplary embodiment of an irradiation device according to the invention.

FIG. 17 shows a patient P whose head has been inserted into an irradiation device 1 having an irradiation apparatus 6 according to the invention, which can be rotated in the directions W.

Figure 18:
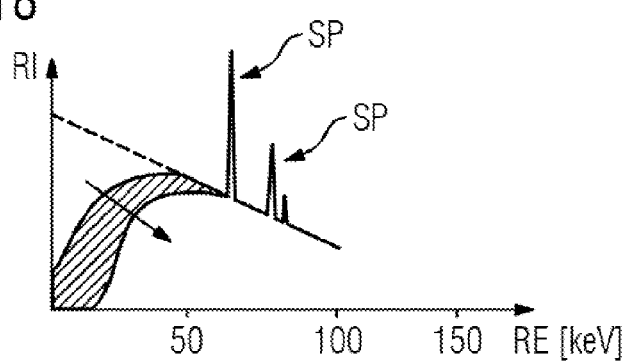
FIG. 18 is a signal diagram intended to illustrate an effect produced by the apparatus according to the invention.

FIG. 18 shows a diagram intended to illustrate the effect produced by the filter apparatus 3 according to the invention. FIG. 18 plots an x-ray intensity RI for different x-ray energies RE of an x-ray radiation source 2. As can be seen from FIG. 18, there is a significant attenuation of the low-energy x-ray spectrum as a result of the filter apparatus 3 according to the invention, as indicated by the hatched area. The characteristic radiation lines or signal peaks SP shown in FIG. 18 remain preserved to the greatest possible extent.

The layer thicknesses of the ferrofluid F within the fluid container 7 can vary. The layer thicknesses for a ferrofluidic layer can lie, for example, in a range of 1 to 10 mm in the case of a typical area on the floor of the fluid container 7 of approximately 10×10 cm. This enables resolutions of the aperture of less than 1 cm to be achieved. In a possible embodiment variant, the percentage by volume of the magnetic particles within the ferrofluid F can be up to 20%.

Figure 19:
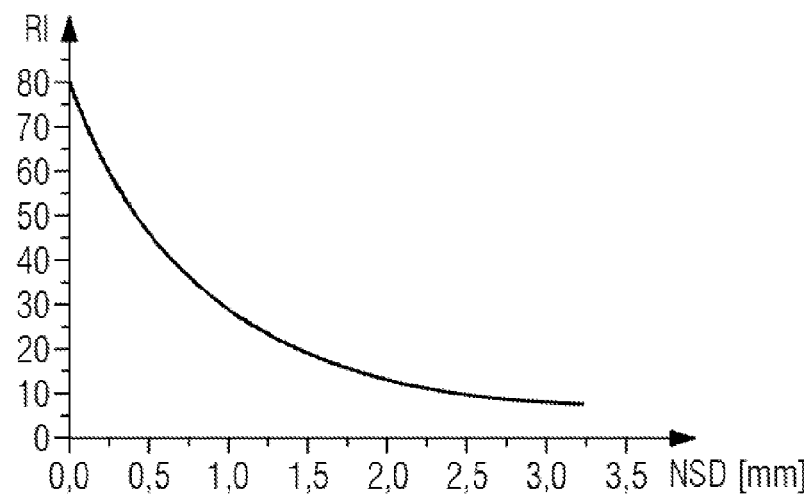
FIG. 19 is a diagram intended to illustrate x-ray absorption properties of a ferrofluid such as can be used with the method and apparatus according to the invention.

FIG. 19 shows a diagram intended to illustrate x-ray absorption properties of a ferrofluid F having a 5% by volume fraction of $Fe_3O_4$. Shown in this case is an x-ray absorption at 70 kV based on 5% ferrofluid at a density of 1.87 g/cm$^3$. In the diagram shown in FIG. 19, the net layer thickness NSD of $Fe_3O_4$ in mm is plotted against x-ray intensity RI. The attenuation coefficient in this case lies at approximately 1.2 mm$^{-1}$, corresponding to 22 mm ferrofluid layer thickness, and the half-value of thickness lies at approximately 0.6 mm net layer thickness of $Fe_3O_4$, corresponding to approximately 12 mm ferrofluid layer thickness.

In addition to its use as a flexible aperture AP, the filter apparatus 3 according to the invention can also be employed as a compensating filter for the dose/area product for two-dimensional projection methods or multirow detection for three-dimensional views, in the field of computed tomography, for example. In this case, the filter properties can be adapted by the composition of the ferrofluid F.

Fluid films having different absorber properties can be used in order, for example, to improve the contrast of an element in an energy-filtering manner by using a differential image. The differential image can be, for example, an x-ray photograph with or without a ferrofluid filter 3. With the filter apparatus 3 according to the invention, applying a magnetic gradient field to the ferrofluid F causes a change in its size, shape and focus relative to a projection axis of a radiation device. This enables the radiation exposure dose for the patient P to be reduced in a targeted manner. By controlling the ferrofluidic aperture or, as the case may be, activating the filter apparatus 3, it is possible to specify an image section in which a high-contrast image, for example an x-ray photograph, is recorded. With the filter apparatus 3 according to the invention, it is possible to vary both the position of an aperture AP and the filter strength or absorption. The filter apparatus 3 according to the invention is suitable, in particular, for irradiation apparatuses for irradiating an object with high-frequency electromagnetic beams, in particular for medical irradiation or imaging devices in which patients P are irradiated with high-frequency electromagnetic beams, in particular with x-rays.

The invention claimed is:

1. A filter apparatus for filtering X-ray radiation, the filter apparatus comprising:
    a fluid container; and
    a ferrofluid disposed in said fluid container; and
    at least one magnet for applying a magnetic gradient field to said ferrofluid;
    said ferrofluid configured to at least partially absorb the X-ray radiation; and
    said ferrofluid having a distribution within said fluid container being laterally variable in a first lateral direction and in a second lateral direction with respect to a direction of the X-ray radiation by the magnetic gradient field applied by said at least one magnet, wherein the second lateral direction is orthogonal to the first lateral direction.

2. The filter apparatus according to claim 1, wherein said ferrofluid has ferromagnetic nanoparticles contained in a carrier medium.

3. The filter apparatus according to claim 1, wherein said carrier medium is oil.

4. The filter apparatus according to claim 2, which further comprises a transparent liquid disposed in said fluid container in addition to said ferrofluid, said transparent liquid being immiscible with said carrier medium of said ferrofluid.

5. The filter apparatus according to claim 4, wherein said transparent liquid is water or alcohol.

6. The filter apparatus according to claim 1, which further comprises magnets disposed around said fluid container and configured to generate the magnetic gradient field.

7. The filter apparatus according to claim 6, wherein said magnets are switchable electromagnets having at least one of:
    an individually adjustable generated field strength or
    a variable distance from said fluid container.

8. The filter apparatus according to claim 6, wherein said magnets are permanent magnets disposed at a variable distance from said fluid container.

9. The filter apparatus according to claim 1, wherein said ferrofluid disposed in said fluid container has a filter property being adjustable with respect to an absorption of the X-ray radiation.

10. The filter apparatus according to claim 9, wherein said filter property of said ferrofluid contained in said fluid container is adjustable with respect to the absorption of the X-ray radiation by:
    selecting magnetic nanoparticles or a mixture of different magnetic nanoparticles; or
    admixing nonmagnetic particles into the ferrofluid; or
    changing a percentage by volume of magnetic and nonmagnetic particles in said ferrofluid and varying a volume of said ferrofluid contained in said fluid container.

11. An irradiation apparatus for irradiating an object with X-ray radiation, the irradiation apparatus comprising:
    a radiation source for generating the X-ray radiation; and
    a filter apparatus according to claim 1.

12. An irradiation device for irradiating an object with X-ray radiation, the irradiation device comprising:
    an irradiation apparatus including a radiation source for generating the X-ray radiation and a filter apparatus according to claim 1;
    a patient receiving compartment for accommodating a patient as an object; and
    a radiation detector disposed in said patient receiving compartment and configured to register the X-ray radiation passing through the patient.

13. The irradiation device according to claim 12, wherein said irradiation apparatus is rotatable around said patient receiving compartment.

14. The irradiation device according to claim 12, wherein said radiation detector has a camera or an exposable film.

15. The irradiation device according to claim 12, wherein said fluid container has a bow-tie geometry.

16. The irradiation device according to claim 12, wherein said distribution of said ferrofluid contained within said fluid container is variable relative to a projection axis of the irradiation device by using the applied magnetic gradient field.

17. The irradiation device according to claim 12, wherein said distribution of said ferrofluid within said fluid container is adjusted as a function of a detected position of the patient disposed in said patient receiving compartment.

18. A method for filtering X-ray radiation, the method comprising:
    obtaining a ferrofluid that at least partially absorbs X-ray radiation; and
    applying a magnetic gradient field to laterally displace a distribution of the ferrofluid in a first lateral direction and in a lateral second direction with respect to a direction of X-ray radiation, wherein the second lateral direction is orthogonal to the first lateral direction.

19. The filter apparatus according to claim 1, wherein said at least one magnet is selected from the group consisting of a plurality of magnets annularly surrounding said fluid container and four magnets surrounding said fluid container.

* * * * *